(12) United States Patent
Shin et al.

(10) Patent No.: US 12,221,509 B2
(45) Date of Patent: Feb. 11, 2025

(54) TETRAARYLBORATE COMPOUND, CATALYST COMPOSITION COMPRISING SAME, AND METHOD FOR PREPARING ETHYLENE HOMOPOLYMERS OR COPOLYMERS OF ETHYLENE AND A-OLEFIN BY USING SAME

(71) Applicant: Sabic SK Nexlene Company Pte. Ltd., Singapore (SG)

(72) Inventors: Dongcheol Shin, Daejeon (KR); Yeonock Oh, Daejeon (KR); Miji Kim, Daejeon (KR)

(73) Assignee: Sabic SK Nexlene Company Pte. Ltd., Singapore (SG)

( * ) Notice: Subject to any disclaimer, the term of this patent is extended or adjusted under 35 U.S.C. 154(b) by 788 days.

(21) Appl. No.: 17/433,268

(22) PCT Filed: Feb. 24, 2020

(86) PCT No.: PCT/IB2020/051519
§ 371 (c)(1),
(2) Date: Aug. 24, 2021

(87) PCT Pub. No.: WO2020/174346
PCT Pub. Date: Sep. 3, 2020

(65) Prior Publication Data
US 2022/0089790 A1 Mar. 24, 2022

(30) Foreign Application Priority Data

Feb. 28, 2019 (KR) .................. 10-2019-0024356
Feb. 20, 2020 (KR) .................. 10-2020-0020828

(51) Int. Cl.
| | | |
|---|---|---|
| C08F 4/6592 | (2006.01) | |
| C07F 5/02 | (2006.01) | |
| C08F 110/02 | (2006.01) | |
| C08F 210/16 | (2006.01) | |

(52) U.S. Cl.
CPC .............. *C08F 4/6592* (2013.01); *C07F 5/02* (2013.01); *C07F 5/027* (2013.01); *C08F 210/16* (2013.01)

(58) Field of Classification Search
CPC ...... C07F 5/027; C08F 5/6592; C08F 110/02; C08F 210/16
See application file for complete search history.

(56) References Cited

U.S. PATENT DOCUMENTS

| | | |
|---|---|---|
| 4,752,597 A | 6/1988 | Turner |
| 5,103,030 A | 4/1992 | Rohrmann et al. |
| 6,268,444 B1 | 7/2001 | Klosin et al. |
| 6,329,478 B1 | 12/2001 | Katayama et al. |
| 6,515,155 B1 | 2/2003 | Klosin et al. |
| 6,555,634 B1 | 4/2003 | Klosin et al. |
| 6,613,850 B1 | 9/2003 | Sato et al. |
| 6,660,816 B2 | 12/2003 | Sato et al. |
| 6,884,857 B1 | 4/2005 | Stevens et al. |
| 7,569,646 B1 | 8/2009 | Canich |
| 9,611,280 B2 | 4/2017 | Takaishi et al. |
| 2001/0008927 A1 | 7/2001 | Sato et al. |
| 2017/0204129 A1 | 7/2017 | Kim et al. |

FOREIGN PATENT DOCUMENTS

| | | |
|---|---|---|
| EP | 0320762 A2 | 6/1989 |
| EP | 0372632 A1 | 6/1990 |
| EP | 0416815 A2 | 3/1991 |
| EP | 0420436 A1 | 4/1991 |
| EP | 0842939 A1 | 5/1998 |
| EP | 0887355 A1 | 12/1998 |
| EP | 0889062 A | 1/1999 |
| JP | 63092621 A | 4/1988 |
| JP | H0284405 A | 3/1990 |
| JP | H03002347 A | 1/1991 |
| KR | 1020000029833 A | 5/2000 |
| KR | 1020160007583 A | 1/2016 |
| RU | 2186073 C2 | 7/2002 |
| RU | 2230067 C2 | 1/2004 |
| WO | 9806728 A1 | 2/1998 |
| WO | 0142315 A1 | 6/2001 |
| WO | 2015183017 A1 | 12/2015 |

OTHER PUBLICATIONS

Mahdi et al., "Stoichiometric and Catalytic Inter- and Intramolecular Hydroamination of Terminal Alkynes by Frustrated Lewis Pairs", Chem. Eur. J., 2015, pp. 11134-11142, vol. 21.
Braunschweig et al., "Constrained geometry complexes—Synthesis and applications", Coordination Chemistry Reviews, 2006, pp. 2691-2720, vol. 250.
Musikabhumma et al., "Tritylpyridinium tetrakis(pentafluorophenyl)borate as an efficient activator for "constrained-geometry" catalysts in ethylene polymerization", Journal of Molecular Catalysis A: Chemical, 2004, pp. 73-81, vol. 208.
Nakajima et al., "Diaryl-lambda(3)-chloranes: Versatile Synthesis and Unique Reactivity as Aryl Cation Equivalent", Journal of the American Chemical Society, 2019, pp. 6499-6503, vol. 141.

*Primary Examiner* — Caixia Lu
(74) *Attorney, Agent, or Firm* — The Webb Law Firm

(57) ABSTRACT

Provided is a novel tetraarylborate compound, a catalyst composition including the same, and a method for preparing an ethylene homopolymer or an ethylene-α-olefin copolymer using the same. Specifically, the teraarylborate compound having excellent thermal stability, able to be completely dissolved in an aliphatic hydrocarbon-based solvent to facilitate the operation of commercial processes and effectively inducing the activation of a single active site catalyst, may be used as a catalyst activator to provide an ethylene-based copolymer selected from a high molecular weight ethylene homopolymer and ethylene-α-olefin copolymer having high catalyst activity.

15 Claims, No Drawings

TETRAARYLBORATE COMPOUND, CATALYST COMPOSITION COMPRISING SAME, AND METHOD FOR PREPARING ETHYLENE HOMOPOLYMERS OR COPOLYMERS OF ETHYLENE AND A-OLEFIN BY USING SAME

CROSS-REFERENCE TO RELATED APPLICATIONS

This application is the United States national phase of International Application No. PCT/IB2020/051519 filed Feb. 24, 2020, and claims priority to Korean Patent Application Nos. 10-2019-0024356 filed Feb. 28, 2019 and 10-2020-0020828 filed Feb. 20, 2020, the disclosures of which are hereby incorporated by reference in their entirety.

BACKGROUND OF THE INVENTION

Field of the Invention

The present invention relates to a tetraarylborate compound, a catalyst composition including the same, and a method for preparing an ethylene homopolymer or an ethylene-α-olefin copolymer using the same.

Description of Related Art

Conventionally, in the preparation of an ethylene homopolymer or an ethylene-α-olefin copolymer, a so-called Ziegler-Natta catalyst system including a main catalyst component of a titanium or vanadium compound, and a cocatalyst component of an alkyl aluminum compound has been used. However, though the Ziegler-Natta catalyst system has high activity in ethylene polymerization, it has demerits in that, generally a produced polymer has a broad molecular weight distribution due to a heterogeneous catalyst active site, and in particular, an ethylene-α-olefin copolymer has a non-uniform composition distribution.

Recently, a so-called metallocene catalyst system including a metallocene compound of Group 4 transition metals in the periodic table such as titanium, zirconium and hafnium, and methylaluminoxane as a cocatalyst has been developed. Since the metallocene catalyst system is a homogeneous catalyst having a single catalyst active site, it has properties that polyethylene having a narrow molecular weight distribution and a uniform composition distribution as compared to the conventional Ziegler-Natta catalyst system can be prepared. For example, Patent Document 1 to Patent Document 10 disclose that a metallocene compound is activated with a cocatalyst, methylaluminoxane to polymerize ethylene with high activity, thereby preparing polyethylene having a molecular weight distribution (Mw/Mn) in a range of 1.5 to 2.0. However, it is difficult to obtain a high molecular weight polymer with the catalyst system. In particular, it is known that when the catalyst system is applied to a solution polymerization method carried out at a high temperature of 100° C. or more, a polymerization activity is rapidly reduced, and a β-dehydrogenation reaction is predominant, and thus, the catalyst system is not suitable for preparing a high molecular weight polymer having a weight average molecular weight (Mw) of 100,000 or more.

Meanwhile, as a catalyst system capable of preparing a high molecular weight polymer having high catalyst activity in homopolymerization of ethylene or copolymerization of ethylene and an α-olefin under solution polymerization conditions, a so-called constrained geometry non-metallocene-based catalyst (also known as a single active site catalyst) having a transition metal connected in the form of a ring has been published. Patent Document 11 and Patent Document 12 suggest an example in which an amide group is linked to one cyclopentadiene ligand in the form of a ring, and Patent Document 13 shows an example of a catalyst which links a phenol-based ligand to a cyclopentadiene ligand in the form of a ring, as an electron donating compound. Though this constrained geometric catalyst has significantly improved reactivity with higher α-olefins due to the lowered steric hindrance effect of the catalyst itself, it is commercially important to study a catalyst which provides excellent activity, excellent copolymerization properties, and the like at a high temperature, and a method for activating the catalyst.

In addition, as part of a study on a catalyst system capable of preparing a polymer having high molecular and high catalyst activity in an ethylene homopolymer or an ethylene-α-olefin copolymer under solution polymerization conditions, Patent Document 14 to Patent Document 17 disclose a catalyst system including a cocatalyst provided in a dispersed or slurry state. The cocatalysts disclosed in the Patent Documents above are supplied to the reactor as a catalyst solution containing a toluene solution, etc., and are supplied to the reactor continuously or discontinuously with the metallocene compound. In the case of employing a catalyst system provided in a solid state, it may cause a failure in a supply device such as a pump used in a production process on a large scale, which may interrupt a stable operation. In addition, since an aromatic hydrocarbon-based solvent such as toluene is required to be used in terms of the solubility of the catalyst system, it remains in an ethylene homopolymer or an ethylene-α-olefin copolymer, and the like, that is the final product, to cause odors, and thus an additional process for removing thereof is required. Under the background of such study, there is a continuing need for studies to solve the problems of the catalyst system described above and to provide a catalyst system capable of preparing a high molecular weight polymer having high catalyst activity in homopolymerization of ethylene or copolymerization of ethylene and an α-olefin under solution polymerization conditions.

(Patent Document 1) European Patent Application Publication No. 320,762 (Jun. 21, 1989)

(Patent Document 2) European Patent Application Publication No. 372,632 (Jun. 13, 1990)

(Patent Document 3) Japanese Patent Laid-Open Publication No. (Sho) 63-092621 (Apr. 23, 1988)

(Patent Document 4) Japanese Patent Laid-Open Publication No. (Hei) 02-84405 (Mar. 26, 1990)

(Patent Document 5) Japanese Patent Laid-Open Publication No. (Hei) 03-2347 (Jan. 8, 1991)

(Patent Document 6) European Patent Publication No. 0416815 (Mar. 13, 1991)

(Patent Document 7) European Patent Publication No. 0420436 (Apr. 3, 1991)

(Patent Document 8) European Patent Publication No. 0842939 (May 20, 1998)

(Patent Document 9) WO 98/06728 (Feb. 19, 1998)

(Patent Document 10) WO 01/42315 (Jun. 14, 2001)

(Patent Document 11) European Patent Publication No. 0416815 (Aug. 13, 1997)

(Patent Document 12) European Patent Publication No. 0420436 (Aug. 14, 1996)

(Patent Document 13) European Patent Publication No. 0842939 (May 20, 1998)

(Patent Document 14) European Patent Publication No. 0889062 (Jan. 7, 1999)

(Patent Document 15) European Patent Publication No. 0887355 (Dec. 30, 1998)

(Patent Document 16) U.S. Pat. No. 6,613,850 (Sep. 2, 2003)

(Patent Document 17) U.S. Pat. No. 6,660,816 (Jul. 19, 2001)

SUMMARY OF THE INVENTION

Technical Problem

In order to overcome the above problems of the prior art, the present inventors conducted an extensive study, and as a result, found that a tetraarylborate compound including cations of alkylideneanilinium structures can be used as a cocatalyst to increase the solubility in an aliphatic hydrocarbon-based solvent and to effectively improve the activity of a single active site catalyst, thereby completing the present invention.

An embodiment of the present invention is directed to providing a new tetraarylborate compound that is useful as a cocatalyst for preparing an ethylene homopolymer or an ethylene-α-olefin copolymer, and a catalyst composition including the tetraarylborate compound and a single active site catalyst.

Another embodiment of the present invention is directed to providing a method for preparing an ethylene homopolymer or an ethylene-α-olefin copolymer economically from a commercial point of view, using the catalyst composition.

Technical Solution

In one general aspect, there is provided a tetraarylborate compound represented by the following Formula 1:

[Formula 1]

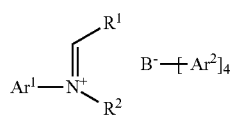

wherein

B is a boron atom;

Ar¹ is (C6-C30)aryl, wherein the aryl of Ar1 may be further substituted by one or more substituents selected from the group consisting of (C1-C30)alkyl, halo(C1-C30)alkyl, and (C6-C30)aryl(C1-C30)alkyl;

Ar² is fluorine-substituted (C6-C30)aryl;

R¹ is hydrogen or (C1-C30)alkyl; and

R² is (C1-C30)alkyl, or R2 and R1 may be linked to each other to form a ring, wherein the ring may be further substituted by one or more substituents selected from the group consisting of (C1-C30)alkyl, (C1-C30)alkoxy, halo (C1-C30)alkyl, (C3-C30)cycloalkyl, (C1-C30)alkyl(C6-C30)aryl, (C6-C30)aryl, (C6-C30)aryloxy, (C1-C30)alkyl (C6-C30)aryloxy, (C6-C30)aryl(C1-C30)alkyl, and ((C1-C30)alkyl(C6-C30)aryl)(C1-C30)alkyl. In another general aspect, there is provided a transition metal catalyst composition for preparing an ethylene homopolymer or an ethylene-α-olefin copolymer including: the tetraarylborate compound of Formula 1; a single active site catalyst including a Group 4 transition metal; and an aluminum compound.

In another general aspect, there is provided a method for preparing an ethylene homopolymer or an ethylene-α-olefin copolymer using the transition metal catalyst composition for preparing the ethylene homopolymer or the ethylene-α-olefin copolymer.

In another general aspect, there is provided a method for preparing an ethylene homopolymer or an ethylene-α-olefin copolymer including: injecting a catalyst activator composition including the tetraarylborate compound of Formula 1 and an organic solvent used in the preparation step of the tetraarylborate compound, without a separating process; injecting a single active site catalyst solution including a Group 4 transition metal; injecting an aluminum compound solution; and injecting ethylene.

Advantageous Effects

The tetraarylborate compound according to the present invention has high solubility in a hydrocarbon-based solvent and has excellent thermal stability to activate a single active site catalyst even at a high temperature. In particular, the tetraaryborate compound may be completely dissolved in an aliphatic hydrocarbon-based solvent and may not be subject to limitation on the amount of use by solubility. In addition, due to such solubility, a solution-type cocatalyst may not only facilitate the operation of a commercial process, but also solve the problems caused by using the cocatalyst that is provided in the dispersed or slurry state, which has been pointed out as a problem of the prior art.

In addition, a solution-type cocatalyst may maintain high catalyst activity even at a high temperature, has excellent copolymerization reactivity with ethylene, α-olefins, other comonomers, and the like, and may prepare a high molecular weight polymer with a high yield. Thus, the solution-type cocatalyst has high in combination with a single active site catalyst such as various metallocenes or non-metallocenes.

Further, when a solution polymerization is carried out at a high temperature, the degree of isomerization of α-olefins having 4 or more carbon atoms can be limited to effectively reduce the consumption of comonomers such as α-olefins. Accordingly, a high molecular weight ethylene-based polymer having various physical properties, that is, an ethylene-based polymer such as an ethylene homopolymer or an ethylene-α-olefin copolymer may be provided more economically.

DESCRIPTION OF THE INVENTION

Hereinafter, the present invention will be described in more detail. Technical terms and scientific terms used herein have the general meaning understood by those skilled in the art to which the present invention pertains, unless otherwise defined, and a description for the known function and configuration unnecessarily obscuring the gist of the present invention will be omitted in the following description.

The term "alkyl" as described herein refers to a monovalent straight-chain or branched-chain saturated hydrocarbon radical consisting of only carbon and hydrogen atoms, and an example of the alkyl radical includes, but is not limited to, methyl, ethyl, propyl, butyl, pentyl, hexyl, heptyl, octyl, nonyl, decyl, dodecyl, tetradecyl, hexadecyl, octadecyl, and the like.

The term "aryl" as described herein refers to an organic radical derived from aromatic hydrocarbon by the removal of one hydrogen, including a monocyclic or fused ring system containing suitably 4 to 7, preferably 5 or 6 ring atoms in each ring, and even a form in which a plurality of aryls are linked by a single bond. A fused ring system may include an aliphatic ring such as saturated or partially saturated rings, and necessarily includes one or more aromatic rings. In addition, the aliphatic ring may contain nitrogen, oxygen, sulfur, carbonyl, and the like in the ring. An example of the aryl radical includes, but not limited to, phenyl, naphthyl, biphenyl, indenyl, fluorenyl, phenanthrenyl, anthracenyl, triphenylenyl, pyrenyl, chrysenyl, naphthacenyl, 9,10-dihydroanthracenyl, and the like.

The term "cycloalkyl" as described herein refers to a monovalent saturated carbocyclic radical composed of one or more rings. An example of the cycloalkyl radical includes, but is not limited to, cyclopropyl, cyclobutyl, cyclopentyl, cyclohexyl, cycloheptyl, and the like.

The term "halo" or "halogen" as described herein refers to fluorine, chlorine, bromine, iodine, or the like.

The term "haloalkyl" as described herein refers to alkyl substituted by one or more halogens, and an example thereof may include, but is not limited to, trifluoromethyl and the like.

The term "fluorine-substituted aryl" as described herein refers to aryl substituted by one or more fluorine atoms, wherein "aryl" is as defined above.

The term "arylalkyl" as described herein refers to alkyl substituted by one or more aryls, and an example thereof may include, but is not limited to, benzyl and the like.

The terms "alkoxy" and "aryloxy" refer to an *—O-alkyl radical and an *—O-aryl radical, respectively, wherein "alkyl" and "aryl" are as defined above.

The term "catalyst activator" as described herein may be interpreted in the same meaning as the cocatalyst, and the catalyst activator specifically described herein may be a compound represented by the following Formula 1.

Catalyst activators, including ionic salts, for the activation of a single active site catalyst typically have the form of ionic salts. With such structural features, the catalyst activators are highly insoluble in an aliphatic hydrocarbon-based solvent, and are dissolved only to a small extent in an aromatic hydrocarbon-based solvent.

Furthermore, a monomer for the preparation of an ethylene-based polymer such as an ethylene homopolymer or an ethylene-α-olefin copolymer, is preferably polymerized in an aliphatic hydrocarbon-based solvent in order to reduce the miscibility with the solvent and the content of the aromatic hydrocarbon in the obtained ethylene-based polymer, however, the aromatic hydrocarbon-based solvent was inevitably used due to the problems described above.

Further, when an aromatic hydrocarbon-based solvent such as toluene is used, it remains in the resulting high molecular weight ethylene homopolymer or ethylene-α-olefin copolymer, causing inferior polymer properties or unpleasant odors.

In view of these problems of the prior art, the applicant has repeatedly conducted studies for a catalyst activator including ionic salts which may be capable of solution polymerization in an aliphatic hydrocarbon-based solvent, and as a result, has devised a novel tetraarylborate compound having cations of alkylideneanilinium structure.

Such a tetraarylborate compound having cations of alkylideneanilinium structure also has high solubility in a cyclic aliphatic hydrocarbon-based solvent as well as a linear aliphatic hydrocarbon-based solvent. Accordingly, the tetraarylborate compound is suitable for use in a continuous solution process in which a control of a specific amount of a catalyst activator is required. In particular, when the tetraarylborate compound is included, an isomerization reaction of α-olefins is effectively limited.

In addition, the tetraarylborate compound having cations of alkylideneanilinium structure is excellent in high temperature stability to exert an excellent effect on catalyst activity even at a high temperature polymerization temperature of 160° C. or more and enable its commercial operation, thereby having a high industrial utilization value.

Hereinafter, a tetraarylborate compound according to the present invention and a catalyst composition including the same will be described in detail.

The tetraarylborate compound according to an exemplary embodiment of the present invention may be represented by the following Formula 1:

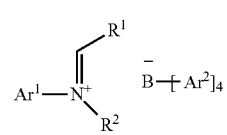

[Formula 1]

wherein

B is a boron atom;

$Ar^1$ is (C6-C30)aryl, wherein the aryl of $Ar^1$ may be further substituted by one or more substituents selected from the group consisting of (C1-C30)alkyl, halo(C1-C30)alkyl, and (C6-C30)aryl(C1-C30)alkyl;

$Ar^2$ is fluorine-substituted (C6-C30)aryl;

$R^1$ is hydrogen or (C1-C30)alkyl; and $R^2$ is (C1-C30)alkyl, or $R^2$ and $R^1$ may be linked to each other to form a ring, wherein the ring may be further substituted by one or more substituents selected from the group consisting of (C1-C30)alkyl, (C1-C30)alkoxy, halo (C1-C30)alkyl, (C3-C30)cycloalkyl, (C1-C30)alkyl(C6-C30)aryl, (C6-C30)aryl, (C6-C30)aryloxy, (C1-C30)alkyl (C6-C30)aryloxy, (C6-C30)aryl(C1-C30)alkyl, and ((C1-C30)alkyl(C6-C30)aryl)(C1-C30)alkyl.

As described above, the tetraarylborate compound has a use of a catalyst activator for the activation of a main catalyst for the preparation of an ethylene homopolymer or an ethylene-α-olefin copolymer. Specifically, the tetraarylborate compound includes cations of alkylideneanilinium structure, thereby implementing improved solubility in an aliphatic hydrocarbon-based solvent. Accordingly, it exhibits enhanced catalyst activity under solution polymerization conditions, particularly continuous solution polymerization conditions, in an aliphatic hydrocarbon-based solvent for the preparation of an ethylene homopolymer or an ethylene-α-olefin copolymer.

Specifically, the tetraarylborate compound may be represented by the following Formula 2 or Formula 3:

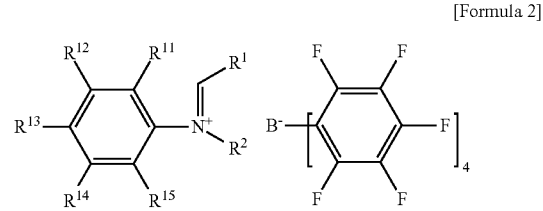

[Formula 2]

wherein

B, $R^1$, and $R^2$ are as defined in Formula 1 of claim 1; and $R^{11}$ to $R^{15}$ are each independently hydrogen, (C1-C30) alkyl, halo(C1-C30)alkyl, or (C6-C30)aryl(C1-C30)alkyl;

[Formula 3]

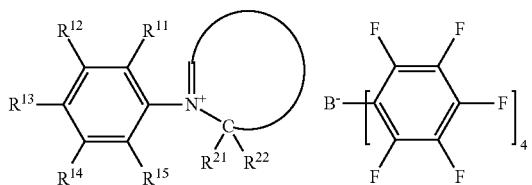

wherein

B is as defined in Formula 1 of claim 1;

$R^{11}$ to $R^{15}$ are each independently hydrogen, (C1-C30)alkyl, halo(C1-C30)alkyl, or (C6-C30)aryl(C1-C30)alkyl;

n is an integer selected from 2 to 6; and $R^{21}$ and $R^{22}$ are each independently hydrogen, (C1-C30)alkyl, (C1-C30)alkoxy, halo(C1-C30)alkyl, (C3-C30)cycloalkyl, (C1-C30)alkyl(C6-C30)aryl, (C6-C30)aryl, (C6-C30)aryloxy, (C1-C30)alkyl(C6-C30)aryloxy, (C6-C30)aryl(C1-C30)alkyl, or ((C1-C30)alkyl(C6-C30)aryl)(C1-C30)alkyl.

More specifically, in Formula 1, at least one selected from $R^1$ and $R^2$ may be a long chain alkyl, that is, (C8-C30)alkyl.

As an example, in Formula 2, $R^{11}$ to $R^{15}$ may be each independently hydrogen or (C1-C30)alkyl; at least one selected from $R^1$ and $R^2$ may be a long chain alkyl, wherein $R^1$ may be hydrogen or (C8-C30)alkyl, and $R^2$ may be (C1-C30)alkyl.

As an example, in Formula 2, $R^{11}$ to $R^{15}$ may be each independently hydrogen or (C1-C7)alkyl; at least one selected from $R^1$ and $R^2$ may be a long chain alkyl, wherein $R^1$ may be hydrogen or (C8-C30)alkyl, and $R^2$ may be (C8-C30)alkyl.

As an example, in Formula 2, $R^{11}$ to $R^{15}$ may be each independently hydrogen, methyl, or ethyl; at least one selected from $R^1$ and $R^2$ may be a long chain alkyl, wherein $R^1$ may be hydrogen or (C8-C30)alkyl, and $R^2$ may be (C8-C30)alkyl.

As an example, in Formula 3, $R^{11}$ to $R^{15}$ may be each independently hydrogen or (C1-C30)alkyl; n may be an integer selected from 2 to 4; and $R^{21}$ and $R^{22}$ may be each independently hydrogen or (C8-C30)alkyl.

As an example, in Formula 3, $R^{11}$ to $R^{15}$ may be each independently hydrogen or (C1-C7)alkyl; n may be an integer of 3 or 4; and $R^{21}$ and $R^{22}$ may be each independently hydrogen or (C8-C30)alkyl.

As an example, in Formula 3, $R^{11}$ to $R^{15}$ may be each independently hydrogen or (C1-C7)alkyl; n may be an integer of 3 or 4; and $R^{21}$ and $R^{22}$ may be each independently hydrogen or (C1-C7)alkyl.

As an example, in Formula 3, $R^{11}$ to $R^{15}$ may be each independently hydrogen, methyl, or ethyl; n may be an integer of 3 or 4; and $R^{21}$ and $R^{22}$ may be each independently hydrogen or (C8-C30)alkyl.

Most specifically, in Formula 1, $R^1$ and $R^2$ may be each independently (C12-C30)alkyl.

As an example, in Formula 2, $R^{11}$ to $R^{15}$ may be each independently hydrogen, methyl, or ethyl; and $R^1$ and $R^2$ may be (C12-C30)alkyl.

As an example, in Formula 3, $R^{11}$ to $R^{15}$ may be each independently hydrogen, methyl, or ethyl; n may be an integer of 3 or 4; and $R^{21}$ and $R^{22}$ may be each independently hydrogen or (C12-C30)alkyl, wherein at least one of $R^{21}$ and $R^{22}$ may be (C12-C30)alkyl.

As an example, in Formula 1, $R^1$ may be (C15-C25) alkyl, and $R^2$ may be (C16-C26)alkyl.

As an example, in Formula 1, $R^1$ may be (C15-C17) alkyl, and $R^2$ may be (C16-C18)alkyl.

In addition, an specific aspect of the tetraarylborate compound represented by Formula 1 may include, but is not limited to, N-methyl-N-methylideneanilinium tetrakis(pentafluorophenyl)borate, 4-methyl-N-octadecyl-N-octadecylideneanilinium tetrakis(pentafluorophenyl)borate, N-butyl-N-butylideneanilinium tetrakis(pentafluorophenyl)borate, N-tetradecyl-N-tetradecylideneanilinium tetrakis(pentafluorophenyl)borate, N-hexadecyl-N-hexadecylideneanilinium tetrakis(pentafluorophenyl)borate, and N-octadecyl-N-octadecylideneanilinium tetrakis(pentafluorophenyl)borate and the like.

Preferably, an example of the tetraarylborate compound may include N-tetradecyl-N-tetradecylideneanilinium tetrakis(pentafluorophenyl)borate, N-hexadecyl-N-hexadecylideneanilinium tetrakis(pentafluorophenyl)borate, 4-methyl-N-octadecyl-N-octadecylideneanilinium tetrakis(pentafluorophenyl)borate, and N-octadecyl-N-octadecylideneanilinium tetrakis(pentafluorophenyl)borate and the like, and more preferably, an example of the tetraarylborate compound may include N-tetradecyl-N-tetradecylideneanilinium tetrakis(pentafluorophenyl)borate, N-hexadecyl-N-hexadecylideneanilinium tetrakis(pentafluorophenyl)borate, N-octadecyl-N-octadecylideneanilinium tetrakis(pentafluorophenyl)borate, and the like.

The tetraarylborate compound according to an exemplary embodiment of the present invention may be used as a catalyst activator for preparing an ethylene homopolymer and an ethylene-based copolymer selected from an ethylene-α-olefin copolymer, and the like. The tetraarylborate compound has a significantly high solubility in an aliphatic hydrocarbon-based solvent as well as an aromatic hydrocarbon-based solvent. Furthermore, the tetraarylborate compound may be uniformly dissolved and used in an aliphatic hydrocarbon-based solvent, and thus, it is possible to realize stable operation of the production process as well as to implement improved catalyst activity.

In addition, even when the tetraarylborate compound is applied to a solution polymerization method carried out at a high temperature of 100° C. or more, it may be advantageous in preparing a high molecular weight polymer with stable catalyst activity.

In addition, the tetraarylborate compound according to an exemplary embodiment of the present invention may be prepared by reacting a compound represented by the following Formula 4 with a compound represented by the following Formula 5 in the hydrocarbon-based solvent. Here, the tetraarylborate compound may be used as a catalyst activator without separation and purification.

[Formula 1]

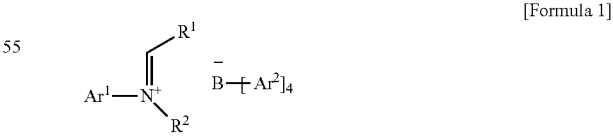

[Formula 4]

[Formula 5]

wherein

B is a boron atom;

$Ar^1$ is (C6-C30)aryl, wherein the aryl of $Ar^1$ may be further substituted by one or more substituents selected from the group consisting of (C1-C30)alkyl, halo(C1-C30)alkyl, and (C6-C30)aryl(C1-C30)alkyl;

$Ar^2$ is fluorine-substituted (C6-C30)aryl;

$R^1$ is hydrogen or (C1-C30)alkyl;

R is (C1-C30)alkyl, wherein R has one greater carbon atom than $R^1$, and when $R^1$ is hydrogen, R has 0 carbon atoms; and $R^2$ is (C1-C30)alkyl, or $R^2$ and $R^1$ may be linked to each other to form a ring, wherein the ring may be further substituted by one or more substituents selected from the group consisting of (C1-C30)alkyl, (C1-C30)alkoxy, halo (C1-C30)alkyl, (C3-C30)cycloalkyl, (C1-C30)alkyl(C6-C30)aryl, (C6-C30)aryl, (C6-C30)aryloxy, (C1-C30)alkyl (C6-C30)aryloxy, (C6-C30)aryl(C1-C30)alkyl and ((C1-C30)alkyl(C6-C30)aryl)(C1-C30)alkyl.

As an example, the hydrocarbon-based solvent may be one or a mixed solvent of two or more selected from a linear aliphatic hydrocarbon-based solvent selected from the group consisting of n-pentane, i-pentane, n-hexane, i-hexane, n-heptane, i-heptane, n-octane, i-octane, n-nonane, i-nonane, n-decane, and i-decane; a cyclic aliphatic hydrocarbon-based solvent selected from the group consisting of cyclopentane, cyclohexane, methylcyclohexane, dimethylcyclohexane, ethylcyclohexane, p-menthane, and decahydronaphthalene; and an aromatic hydrocarbon-based solvent selected from the group consisting of benzene, toluene, and xylene.

As an example, the reaction may be carried out under conditions of a temperature of 0 to 50° C.

As an example, the reaction may be carried out for 10 to 120 minutes, however, there is no limitation as long as the solution in the dispersion or slurry state is completely dissolved during the reaction.

As described above, the tetraarylborate compound according to an exemplary embodiment of the present invention exerts an excellent effect on activating a single active site catalyst. Specifically, the single active site catalyst may be a metallocene catalyst.

As an example, the single active site catalyst may include a Group 4 transition metal in the periodic table, and these transition metals may also be present in formal oxidation state of +2, +3 or +4.

As an example, ligands suitable for the single active site catalyst may include an anionic delocalized n-bonded group, and the anionic delocalized n-bonded group may include a cyclic compound selected from cyclopentadienyl derivatives, indenyl derivatives and fluorenyl derivatives.

Specifically, the transition metal catalyst composition for preparing an ethylene homopolymer or an ethylene-α-olefin copolymer according to an exemplary embodiment of the present invention may include the tetraarylborate compound described above; a single active site catalyst including a Group 4 transition metal; and an aluminum compound and the like.

More specifically, the single active site catalyst may be represented by the following Formula A. The single active site catalyst is a transition metal compound based on an indenyl group having a nitrogen-containing substituent introduced thereto, and has a structure in which a Group 4 transition metal in the periodic table as a center metal is linked by an indene or the derivative group thereof having a rigid plane structure with abundant and widely delocalized electrons and a nitrogen-containing substituent introduced thereto; and an amido group having a substituted silyl group. In particular, the single active site catalyst has a structural characteristic including both an alkyl group or alkenyl group and an aryl group which induce improved solubility in a general hydrocarbon-based solvent, greatly increased activity at high temperature, and a narrow molecular weight distribution, not a broad molecular weight distribution which is a deficiency of diastereomers, in the silyl group linking the indene having a nitrogen-containing substituent introduced thereto or the derivative group thereof and the amido group, and thus, it is advantageous in obtaining elevated catalyst efficiency and a high molecular weight ethylene-based copolymer at a high temperature, in combination with the catalyst activator or the catalyst activator composition according to the invention.

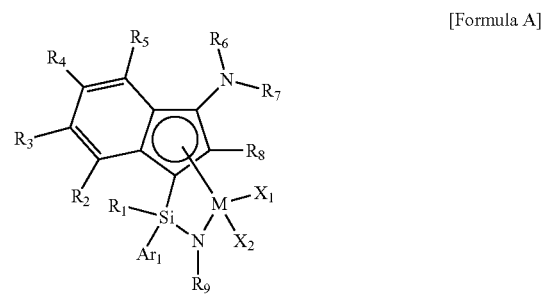

[Formula A]

wherein

M is a Group 4 transition metal in the periodic table;

$R_1$ is (C1-C30)alkyl or (C2-C20)alkenyl, wherein the alkyl or alkenyl of $R_1$ may be further substituted by one or more substituents selected from the group consisting of halogen, (C6-C30)aryl, and (C1-C30)alkyl(C6-C30)aryl;

$Ar_1$ is (C6-C30)aryl, wherein the aryl of $Ar_1$ may be further substituted by one or more substituents selected from the group consisting of (C1-C30)alkyl, halo(C1-C30)alkyl, and (C6-C30)aryl(C1-C30)alkyl;

$R_2$ to $R_5$ are each independently hydrogen, (C1-C30)alkyl, (C1-C30)alkoxy, halo(C1-C30)alkyl, (C3-C20)cycloalkyl, (C1-C30)alkyl(C6-C30)aryl, (C6-C30)aryl, (C6-C30)aryloxy, (C1-C30)alkyl(C6-C30)aryloxy, (C6-C30)aryl(C1-C30)alkyl, or ((C1-C30)alkyl(C6-C30)aryl)(C1-C30)alkyl, or $R_2$ to $R_5$ are linked to an adjacent substituent to form a fused ring, wherein the fused ring may be further substituted by one or more substituents selected from the group consisting of (C1-C30)alkyl, (C1-C30)alkoxy, halo (C1-C30)alkyl, (C3-C20)cycloalkyl, (C1-C30)alkyl(C6-C30)aryl, (C6-C30)aryl, (C6-C30)aryloxy, (C1-C30)alkyl (C6-C30)aryloxy, (C6-C30)aryl(C1-C30)alkyl, and ((C1-C30)alkyl(C6-C30)aryl)(C1-C30)alkyl;

$R_9$ is (C1-C30)alkyl, (C3-C20)cycloalkyl or (C6-C30)aryl (C1-C30)alkyl;

$R_6$ and $R_7$ are each independently (C1-C30)alkyl, halo (C1-C30)alkyl, (C3-C20)cycloalkyl, (C6-C30)aryl, (C1-C30)alkyl(C6-C30)aryl, (C1-C30)alkoxy(C6-C30)aryl or (C6-C30)aryl(C1-C30)alkyl, or $R_6$ and $R_7$ may be linked to each other to form a ring, wherein the ring may be further substituted by one or more substituents selected from the group consisting of (C1-C30)alkyl, halo(C1-C30)alkyl, (C6-C30)aryl(C1-C30)alkyl, (C1-C30)alkoxy, (C3-C20)cycloalkyl, (C6-C20)aryl, (C1-C30)alkyl(C6-C30)aryl and (C6-C20)aryloxy;

$R_8$ is hydrogen or (C1-C30)alkyl;

$X_1$ and $X_2$ are each independently halogen, (C1-C30) alkyl, (C2-C20)alkenyl, (C3-C20)cycloalkyl, (C6-C30)aryl, (C6-C30)aryl(C1-C30)alkyl, ((C1-C30)alkyl(C6-C30)aryl) (C1-C30)alkyl, (C1-C30)alkoxy, (C6-C30)aryloxy, (C1-C30)alkyl(C6-C30)aryloxy, (C1-C30)alkoxy(C6-C30)aryloxy, —OSiR$^a$R$^b$R$^c$, —SR$^d$, NR$^e$R$^f$, —PR$^g$R$^h$, or (C1-C30)alkylidene;

R$^a$ to R$^d$ are each independently (C1-C30)alkyl, (C6-C20)aryl, (C6-C20)aryl(C1-C30)alkyl, (C1-C30)alkyl(C6-C20)aryl, or (C3-C20)cycloalkyl; and R$^e$ to R$^h$ are each independently (C1-C30)alkyl, (C6-C20)aryl, (C6-C20)aryl(C1-C30)alkyl, (C1-C30)alkyl(C6-C20)aryl, (C3-C20)cycloalkyl, tri(C1-C30)alkylsilyl, or tri(C6-C20)arylsilyl;

with a proviso that when one of $X_1$ and X2 is (C1-C30)alkylidene, the other one is ignored.

An indene-based transition metal compound of the present invention is a single active site catalyst having a structural characteristic including both the alkyl group or alkenyl group and the aryl group in the silyl group linking the indenyl group having a nitrogen-containing substituent introduced thereto and the amido group, and thus, has a structural characteristic having both the merit of the alkyl group or alkenyl group which is advantageous in terms of activity and solubility, and the merit of the aryl group having a good injection property of a higher α-olefin. In addition, due to the structural characteristic including both the alkyl group or alkenyl group and the aryl group in the silyl group, it was confirmed by H$^1$-NMR that two types of diastereomers are present. The catalysts developed in the present invention represent characteristics such as preparing a polymer having a narrow molecular weight distribution despite the presence of diastereomers at a ratio of 1:1 to 1:8, and representing high activity even at a high temperature, and is more synergistic in combination with the catalyst activator or catalyst activator composition of the present invention described above. Conventionally, it has been previously reported that the catalysts having diastereomers having an indenyl group and an amido group linked by a silyl group have a characteristic of a broad molecular weight distribution. However, when the indene-based transition metal compound of the present invention, and a catalyst activator or catalyst activator composition are used in combination, an ethylene-based copolymer having a narrow molecular weight distribution could be obtained at high temperature with a high yield. In particular, the catalyst may have a great commercial value, since a high molecular weight ethylene-based copolymer which suppresses the generation of isomers that make polymerization control difficult and has a characteristic of a narrow molecular weight distribution and a narrow composition distribution may be obtained; and an ethylene-based copolymer having a characteristic of a narrow molecular weight distribution and a broad chemical composition distribution may be obtained, by various combinations with the catalyst activator or the catalyst activator composition described above.

In the transition metal catalyst composition for preparing an ethylene homopolymer or an ethylene-α-olefin copolymer according to an exemplary embodiment of the present invention, the indene-based transition metal compound of Formula A may be represented by the following Formula B:

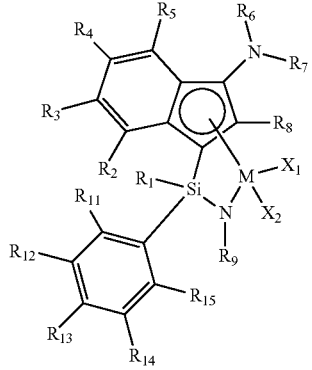

[Formula B]

wherein

M, $R_1$, $R_6$, $R_7$, $R_9$, $X_1$ and $X_2$ are as defined in the above Formula A;

$R_2$ to $R_5$ are each independently hydrogen, (C1-C30)alkyl, (C1-C30)alkoxy, halo(C1-C30)alkyl, (C3-C20)cycloalkyl, (C1-C30)alkyl(C6-C30)aryl, (C6-C30)aryl, (C6-C30)aryloxy, (C1-C30)alkyl(C6-C30)aryloxy, (C6-C30)aryl(C1-C30)alkyl, or ((C1-C30)alkyl(C6-C30)aryl)(C1-C30)alkyl, or $R_2$ to $R_5$ may be linked to an adjacent substituent by (C3-C7)alkylene, (C3-C7)alkenylene or (C4-C7)alkadienylene with or without an aromatic ring to form a fused ring, wherein the fused ring may be further substituted by one or more substituents selected from the group consisting of (C1-C30)alkyl, (C1-C30)alkoxy, halo(C1-C30)alkyl, (C3-C20)cycloalkyl, (C1-C30)alkyl(C6-C30)aryl, (C6-C30)aryl, (C6-C30)aryloxy, (C1-C30)alkyl(C6-C30)aryloxy, (C6-C30)aryl(C1-C30)alkyl and ((C1-C30)alkyl(C6-C30)aryl)(C1-C30)alkyl; and $R_{11}$ to $R_{15}$ are each independently hydrogen, (C1-C30)alkyl, halo(C1-C30)alkyl, or (C6-C30)aryl(C1-C30)alkyl.

In the transition metal catalyst composition for preparing an ethylene homopolymer or an ethylene-α-olefin copolymer according to an exemplary embodiment of the present invention, in the indene-based transition metal compound of Formula A, M is a Group 4 transition metal in the periodic table, and specifically, may be titanium (Ti), zirconium (Zr) or hafnium (Hf), and more specifically, titanium (Ti) or zirconium (Zr).

The (C1-30)alkyl group is, for example, a methyl group, an ethyl group, an n-propyl group, an isopropyl group, an n-butyl group, an isobutyl group, a sec-butyl group, a tert-butyl group, an n-pentyl group, a neopentyl group, an amyl group, an n-hexyl group, an n-octyl group, an n-decyl group, an n-dodecyl group or an n-pentadecyl group; the (C2-C20)alkenyl group is, for example, a vinyl group or an allyl group; the (C3-C20)cycloalkyl group is, for example, a cyclopropyl group, a cyclobutyl group, a cyclopentyl group, a cyclohexyl group, a cycloheptyl group, a cyclooctyl group, a cyclodecyl group or a cyclododecyl group; the (C6-C30)aryl group or (C1-C30)alkyl(C6-C30)aryl group is, for example, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl group, a fluorenyl group, a triphenyl group, a naphthyl group or anthracenyl group; the (C6-C30)aryl(C1-C10)alkyl group or the ((C1-C30)alkyl(C6-C30)aryl)(C1-C30)alkyl group is, for example, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl) methyl group, a (pentamethylphenyl)methyl group, an (ethylphenyl)methyl group, an (n-propylphenyl)methyl group, an (isopropylphenyl)methyl group, an (n-butylphenyl) methyl group, a (sec-butylphenyl)methyl group, a (tert-butylphenyl)methyl group, an (n-pentylphenyl)methyl group, an (neopentylphenyl)methyl group, an (n-hexylphenyl)methyl group, an (n-octylphenyl)methyl group, an (n-decylphenyl)methyl group, an (n-tetradecylphenyl) methyl group, a naphthylmethyl group or an anthracenylmethyl group; the (C1-C30)alkoxy group is, for example, a methoxy group, an ethoxy group, an n-propoxy group, an isopropoxy group, an n-butoxy group, a sec-butoxy group, a tert-butoxy group, an n-pentoxy group, a neopentoxy group, an n-hexoxy group, an n-octoxy group, an n-dodexoxy group, an n-pentadexoxy group or an n-eicoxoxy group.

In the transition metal catalyst composition for preparing an ethylene homopolymer or an ethylene-α-olefin copolymer according to an exemplary embodiment of the present invention, in the indene-based transition metal compound of Formula B, $R_6$ and $R_7$ are each independently (C1-C30) alkyl, (C3-C20)cycloalkyl or (C6-C30)aryl, or $R_6$ and $R_7$ may be linked to (C3-C7)alkylene with or without an aromatic ring to form a ring, wherein the formed ring may be further substituted by one or more substituents selected from the group consisting of (C1-C30)alkyl, (C6-C30)aryl (C1-C30)alkyl, (C1-C30)alkoxy, (C3-C20)cycloalkyl, (C6-C20)aryl, (C1-C30)alkyl(C6-C30)aryl and (C6-C20)aryloxy.

In the transition metal catalyst composition for preparing an ethylene homopolymer or an ethylene-α-olefin copolymer according to an exemplary embodiment of the present invention, in the indene-based transition metal compound of Formula A, $R_1$ may be (C1-C30)alkyl, (C2-C20)alkenyl or (C6-C30)aryl(C1-C30)alkyl; $Ar_1$ may be (C6-C30)aryl or (C1-C30)alkyl(C6-C30)aryl; $R_2$ to $R_5$ may be each independently hydrogen, (C1-C30)alkyl, (C1-C30)alkoxy, (C1-C30) alkyl(C6-C30)aryl, (C6-C30)aryl, (C6-C30)aryloxy, (C1-C30)alkyl(C6-C30)aryloxy or (C6-C30)aryl(C1-C30)alkyl, or $R_2$ to $R_5$ may be linked to an adjacent substituent by (C3-C7)alkylene, (C3-C7)alkenylene or (C4-C7)alkadienylene with or without an aromatic ring to form a fused ring, wherein the fused ring may be further substituted by one or more substituents selected from the group consisting of (C1-C30)alkyl, (C1-C30)alkyl(C6-C30)aryl, (C6-C30) aryl, (C6-C30)aryl(C1-C30)alkyl and ((C1-C30)alkyl(C6-C30)aryl)(C1-C30)alkyl; $R_9$ is (C1-C30)alkyl, (C3-C20)cycloalkyl or (C6-C30)aryl(C1-C30)alkyl; $R_6$ and $R_7$ are each independently (C1-C30)alkyl, (C3-C20)cycloalkyl, (C6-C30)aryl, (C1-C30)alkyl(C6-C30)aryl, (C1-C30)alkoxy (C6-C30)aryl or (C6-C30)aryl(C1-C30)alkyl, or $R_6$ and $R_7$ may be linked to (C3-C7)alkylene with or without an aromatic ring to form a ring, wherein the ring may be further substituted by one or more substituents selected from the group consisting of (C1-C30)alkyl, (C6-C30)aryl(C1-C30) alkyl, (C1-C30)alkoxy, (C3-C20)cycloalkyl, (C6-C20)aryl, (C1-C30)alkyl(C6-C30)aryl and (C6-C20)aryloxy; and $R_8$ may be hydrogen or (C1-C30)alkyl.

In the transition metal catalyst composition for preparing an ethylene homopolymer or an ethylene-α-olefin copolymer according to an exemplary embodiment of the present invention, in the indene-based transition metal compound of Formula A, $R_1$ may be more specifically a methyl group, an ethyl group, an n-propyl group, an isopropyl group, an n-butyl group, a vinyl group, an allyl group or a benzyl group; $Ar_1$ may be more specifically a phenyl group, a naphthyl group, a biphenyl group, a tolyl group, a trimethylphenyl group, a butylphenyl group, a pentylphenyl group, a hexylphenyl group, an octylphenyl group, a decylphenyl group, a dodecylphenyl group or a tetradecylphenyl group; $R_2$ to $R_5$ may be each independently hydrogen, a methyl group, an ethyl group, an n-propyl group, an isopropyl group, an n-butyl group, a phenyl group, a naphthyl group, a biphenyl group, a 2-isopropylphenyl group, a 3,5-xylyl group, a 2,4,6-trimethylphenyl group, a benzyl group, a methoxy group, an ethoxy group, an isopropoxy group, a phenoxy group, a 4-tert-butylphenoxy group or a naphthoxy group; $R_2$ to $R_5$ may be linked to an adjacent substituent by

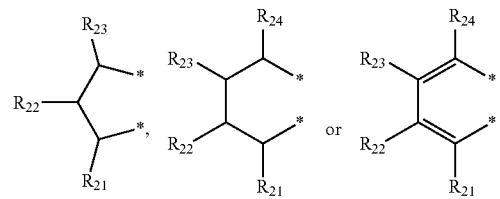

to form a fused ring, $R_{21}$ to $R_{24}$ may be each independently hydrogen, a methyl group, an ethyl group, an n-propyl group, an isopropyl group, an n-butyl group, an isobutyl group, a 2-methylbutyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl group, a fluorenyl group, a triphenyl group, a naphthyl group, an anthracenyl group, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl) methyl group, a (pentamethylphenyl)methyl group, an (ethylphenyl)methyl group, an (n-propylphenyl)methyl group, an (isopropylphenyl)methyl group, an (n-butylphenyl)methyl group, a (sec-butylphenyl)methyl group, a (tert-butylphenyl)methyl group, an (n-pentylphenyl)methyl group, an (neopentylphenyl)methyl group, an (n-hexylphenyl)methyl group, an (n-octylphenyl)methyl group, an (n-decylphenyl)methyl group, an (n-tetradecylphenyl)methyl group, a naphthylmethyl group or an anthracenylmethyl group; $R_9$ may be an isopropyl group, an n-butyl group, an isobutyl group, a 2-methylbutyl group, a sec-butyl group, a tert-butyl group, an n-pentyl group, a cyclopropyl group, a cyclobutyl group, a cyclopentyl group, a benzyl group or a diphenylmethyl group; $R_6$ and $R_7$ may be each independently a methyl group, an ethyl group, an n-propyl group, an isopropyl group, an n-butyl group, an isobutyl group, a 2-methylbutyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl group, a fluorenyl group, a triphenyl, group, a naphthyl group, an anthracenyl group, a benzyl group, a naphthylmethyl group, an anthracenylmethyl group, or a 4-methoxyphenyl group, or $R_6$ and $R_7$ may be linked to

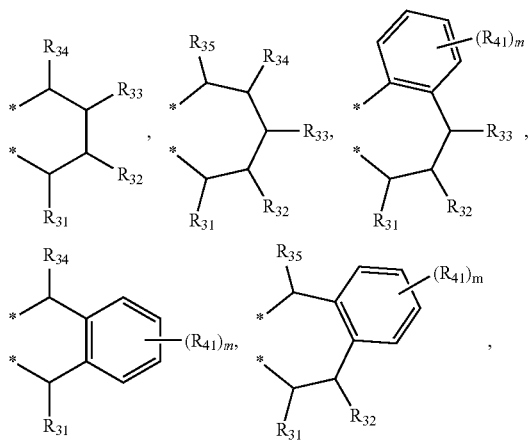

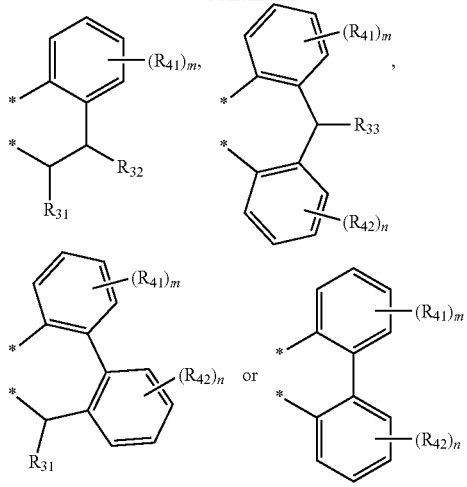

to form a ring; $R_{31}$ to $R_{35}$, $R_{41}$ and $R_{42}$ may be each independently hydrogen, a methyl group, an ethyl group, an n-propyl group, an isopropyl group, an n-butyl group, an isobutyl group, a 2-methylbutyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, an n-propylphenyl group, an isopropylphenyl group, an n-butylphenyl group, a sec-butylphenyl group, a tert-butylphenyl group, an n-pentylphenyl group, a neopentylphenyl group, an n-hexylphenyl group, an n-octylphenyl group, an n-decylphenyl group, an n-dodecylphenyl group, an n-tetradecylphenyl group, a biphenyl group, a fluorenyl group, a triphenyl group, a naphthyl group, an anthracenyl group, a benzyl group, a naphthylmethyl group or an anthracenylmethyl group; m and n may be each independently an integer of 1 to 4; and $R_8$ may be hydrogen, a methyl group, an ethyl group, an n-propyl group, an isopropyl group, an n-butyl group, an isobutyl group, a 2-methylbutyl group or a sec-butyl group.

In the definition of $X_1$ and X2, the halogen atom may be exemplified as fluorine, chlorine, bromine, or iodine, the (C1-C30)alkyl group may be exemplified as a methyl group, an ethyl group, an n-propyl group, an isopropyl group, an n-butyl group, a sec-butyl group, a tert-butyl group, an n-pentyl group, a neopentyl group, an amyl group, an n-hexyl group, an n-octyl group, an n-decyl group, an n-dodecyl group, an n-pentadecyl group, or an n-eicosyl group; the (C3-C20)cycloalkyl group may be exemplified as a cyclopropane group, a cyclobutyl group, a cyclopentyl group, a cyclohexyl group, cycloheptyl group or an adamantyl group; the (C6-C30)aryl group may be exemplified as a phenyl group or a naphthyl group; the (C6-C30)aryl (C1-C30)alkyl group or ((C1-C30)alkyl(C6-C30)aryl)(C1-C30)alkyl group may be exemplified as a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl) methyl group, a (pentamethylphenyl)methyl group, an (ethylphenyl)methyl group, an (n-propylphenyl) methyl group, an (isopropylphenyl)methyl group, an (n-butylphenyl)methyl group, a (sec-butylphenyl)methyl group, a (tert-butylphenyl)methyl group, an (n-pentylphenyl)methyl group, an (neopentylphenyl)methyl group, an (n-hexylphenyl)methyl group, an (n-octylphenyl)methyl group, an (n-decylphenyl)methyl group, an (n-decylphenyl) methyl group, an (n-tetradecylphenyl)methyl group, a naphthylmethyl group or an anthracenylmethyl group; the (C1-C30)alkoxy may be exemplified as a methoxy group, an ethoxy group, an n-propoxy group, an isopropoxy group, an n-butoxy group, a sec-butoxy group, a tert-butoxy group, an n-pentoxy group, a neopentoxy group, an n-hexoxy group, an n-octoxyl group, an n-dodexoxy group, an n-pentadexoxy group or an n-eicoxoxy group; the (C6-C30)aryloxy may be exemplified as a phenoxy group, a 4-tert-butylphenoxy group, or a 4-methoxyphenoxy group; an example of —OSiR$^a$R$^b$R$^c$ may include a trimethylsiloxy group, a triethylsiloxy group, a tri-n-propylsiloxy group, a tripropylsiloxy group, a tri-n-butylsiloxy group, a tri-sec-butylsiloxy group, a tri-tert-butylsiloxy group, a tri-isobutylsiloxy group, a tert-butyldimethylsiloxy group, a tri-n-pentylsiloxy group, a tri-n-hexylsiloxy group or a tricyclohexylsiloxy group, an example of —NR$^e$R$^f$ may include a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a dibenzylamino group, a methylethylamino group, a methylphenylamino group, a benzylhexylamino group, a bistrimethylsilylamino group or a bis-tert-butyldimethylsilylamino group; an example of —PR$^g$R$^h$ may include a dimethylphosphine group, a diethylphosphine group, a di-n-propylphosphine group, a diisopropylphosphine group, a di-n-butylphosphine group, a di-sec-butylphosphine group, a di-tert-butylphosphine group, a diisobutylphosphine group, a tert-butylisopropylphosphine group, a di-n-hexylphosphine group, a di-n-octylphosphine group, a di-n-decylphosphine group, a diphenylphosphine group, a dibenzylphosphine group, a methylethylphosphine group, a methylphenylphosphine group, a benzylhexylphosphine group, a bistrimethylsilylphosphine group or a bis-tert-butyldimethylsilylphosphine group; and an example of —SR$^d$ may include a methylthio group, an ethylthio group, a propylthio group, an isopropylthio group, a 1-butylthio group, or an isopentylthio group.

In the transition metal catalyst composition for preparing an ethylene homopolymer or an ethylene-α-olefin copolymer according to an exemplary embodiment of the present invention, in the indene-based transition metal compound of Formula B, specifically, $X_1$ and X2 may be each independently halogen, (C1-C30)alkyl, (C3-C20)cycloalkyl, (C6-C30)aryl, (C6-C30)aryl(C1-C30)alkyl, (C1-C30)alkoxy, (C6-C30)aryloxy, (C1-C30)alkyl(C6-C30)aryloxy, —OSiR$^a$R$^b$R$^c$, —SR$^d$, —NR$^e$R$^f$, or —PR$^g$R$^h$; and R$^a$ to R$^h$ may be each independently (C1-C30)alkyl or (C6-C20)aryl.

In the transition metal catalyst composition for preparing an ethylene homopolymer or an ethylene-α-olefin copolymer according to an exemplary embodiment of the present invention, in the indene-based transition metal compound of Formula B, more specifically, $X_1$ and X2 may be each independently fluorine, chlorine, bromine, a methyl group, an ethyl group, an isopropyl group, an amyl group, a benzyl group, a methoxy group, an ethoxy group, an isopropoxy group, a tert-butoxy group, a phenoxy group, a 4-tert-butylphenoxy group, a trimethylsiloxy group, a tert-butyldimethylsiloxy group, a dimethylamino group, a diphenylamino group, a dimethylphosphine group, a diethylphosphine group, a diphenylphosphine group, an ethylthio group, or an isopropylthio group.

In the transition metal catalyst composition for preparing an ethylene homopolymer or an ethylene-α-olefin copolymer according to an exemplary embodiment of the present invention, in the indene-based transition metal compound of Formula B, most specifically, M is tetravalent titanium, zirconium or hafnium; $R_1$ is (C1-C30)alkyl; $R_{11}$ to $R_{15}$ are each independently hydrogen or (C1-C30)alkyl; $R_2$ to $R_5$ are each independently hydrogen or (C1-C30)alkyl, or $R_2$ to $R_5$ may be linked to an adjacent substituent by

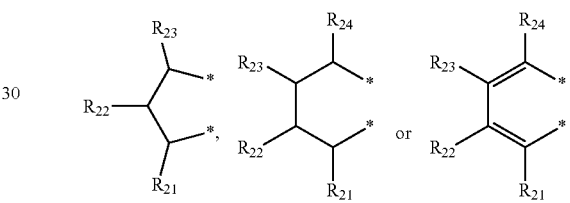

to form a fused ring; $R_{21}$ to $R_{24}$ are each independently hydrogen or (C1-C30)alkyl; $R_6$ and $R_7$ are each independently (C1-C30)alkyl, or $R_6$ and $R_7$ may be linked to

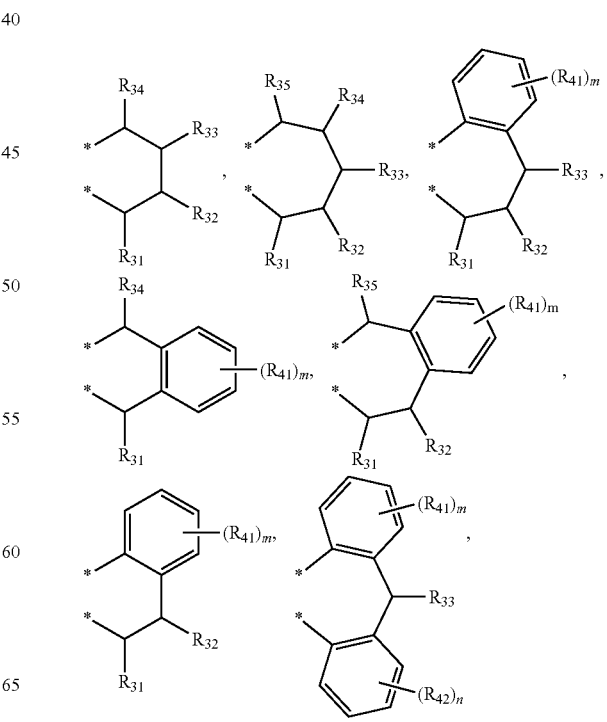

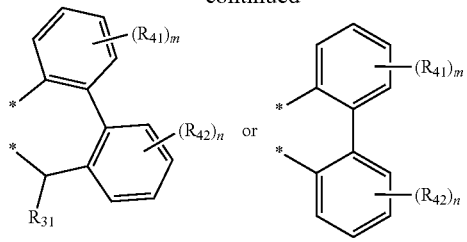

to form a ring; $R_{31}$ to $R_{35}$, $R_{41}$ and $R_{42}$ are each independently hydrogen or (C1-C30)alkyl; m and n are each independently an integer of 1 to 4; $R_9$ is (C1-C30)alkyl or (C3-C20)cycloalkyl; $X_1$ and $X_2$ follow the description of the paragraph above; and $R^a$ to $R^h$ may be each independently (C1-C30)alkyl or (C6-C20)aryl.

In the transition metal catalyst composition for preparing an ethylene homopolymer or an ethylene-α-olefin copolymer according to an exemplary embodiment of the present invention, the indene-based transition metal compound of Formula B may be selected from the compounds having the following structures, but is not limited thereto:

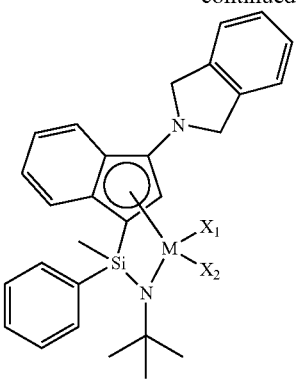

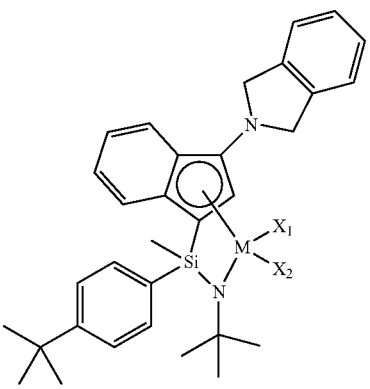

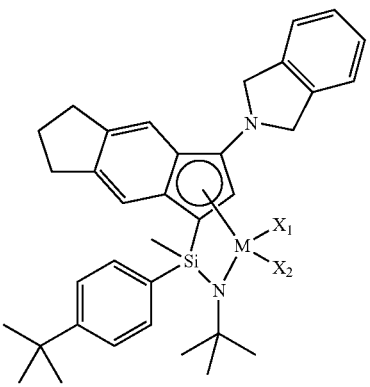

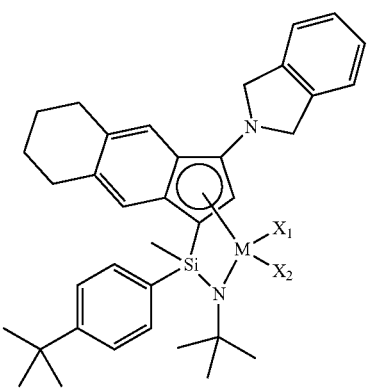

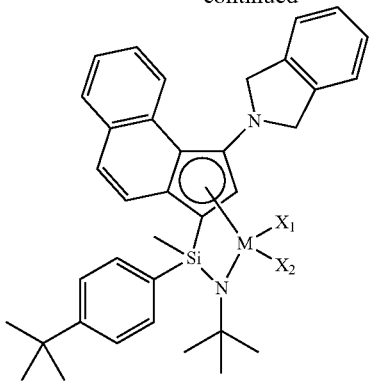

wherein

M is tetravalent titanium, zirconium or hafnium; and $X_1$ and $X_2$ are each independently fluorine, chlorine, bromine, a methyl group, an ethyl group, an isopropyl group, an amyl group, a benzyl group, a methoxy group, an ethoxy group, an isopropoxy group, a tert-butoxy group, a phenoxy group, a 4-tert-butylphenoxy group, a trimethylsiloxy group, a tert-butyldimethylsiloxy group, a dimethylamino group, a diphenylamino group, a dimethylphosphine group, a diethylphosphine group, a diphenylphosphine group, an ethylthio group, or an isopropylthio group.

Meanwhile, the indene-based transition metal compound according to the present invention may preferably operate together with an aluminum compound, a boron compound, or a mixture thereof which may extract an $X_1$ or $X_2$ ligand in the transition metal complex to cationize a center metal, while acting as a counter ion, i.e., an anion having weak binding force, as a cocatalyst, in order to be an active catalyst component which is used for preparation of an ethylene-based polymer selected from the group consisting of an ethylene homopolymer and an ethylene-α-olefin copolymer, and various combinations of the indene-based transition metal compound described above and a catalyst activator or a catalyst activator composition, an aluminum compound, a boron compound or a mixture thereof are also within the scope of the present invention.

In the transition metal catalyst composition for preparing an ethylene homopolymer or an ethylene-α-olefin copolymer according to an exemplary embodiment of the present invention, the aluminum compound may be used as the cocatalyst, and specifically, examples thereof may be one or two or more selected from the group consisting of an aluminoxane compound of the following Formula C or Formula D; an organoaluminum compound of Formula E; and an organoaluminum oxide compound of Formula F or Formula G:

(—Al($R_{51}$)—O—)$_p$     [Formula C]

($R_{51}$)$_2$Al—O—Al($R_{51}$)$_2$     [Formula D]

($R_{52}$)$_{3-r}$Al(E)$_r$     [Formula E]

($R_{53}$)$_2$AlOR$_{54}$     [Formula F]

$R_{53}$Al(OR$_{54}$)$_2$     [Formula G]

wherein $R_{51}$ is (C1-C30)alkyl, preferably a methyl group or an isobutyl group, p is an integer selected from 5 to 20; $R_{52}$ and $R_{53}$ are each independently (C1-C30)alkyl; E is hydrogen or halogen; r is an integer selected from 0 to 3; and $R_{54}$ is (C1-C30)alkyl or (C6-C30)aryl.

Specifically, the aluminum compound may be one or a mixture of two or more selected from alkylaluminoxane and organoaluminum.

A specific example which may be used as the aluminum compound may include methylaluminoxane, modified methylaluminoxane, and tetraisobutylaluminoxane as an aluminoxane compound; trialkylaluminum including trimethylaluminum, triethylaluminum, tripropylaluminum, triisobutylaluminum and trihexylaluminum; dialkylaluminumchloride including dimethylaluminumchloride, diethylaluminumchloride, dipropylaluminum chloride, diisobutylaluminumchloride and dihexylaluminumchloride; alkylaluminumdichloride including methylaluminumdichloride, ethylaluminumdichloride, propylaluminumdichloride, isobutylaluminumdichloride and hexylaluminumdichloride; dialkylaluminum hydride including dimethylaluminum hydride, diethylaluminum hydride, dipropylaluminum hydride, diisobutylaluminum hydride, and dihexylaluminum hydride, as an organic aluminum compound.

More specifically, the aluminum compound may be one or a mixture of two or more selected from the group consisting of an alkylaluminoxane and organoaluminum, and most specifically, one or a mixture of two or more selected from the group consisting of methylaluminoxane, modified methylaluminoxane, tetraisobutylaluminoxane, trimethylaluminum, triethylaluminum, trioctylaluminum, and triisobutylaluminum.

Meanwhile, the aluminum compound may serve as a scavenger which removes impurities acting as a poison to the catalyst in the reactant.

In the transition metal catalyst composition for preparing an ethylene homopolymer or an ethylene-α-olefin copolymer according to an exemplary embodiment of the present invention, a preferred range of the ratio between the indene-based transition metal compound of the present invention and a tetraarylborate compound as a catalyst activator may be 1:0.1 to 100, based on a mole ratio of the transition metal (M):boron atom (B).

In the transition metal catalyst composition for preparing an ethylene homopolymer or an ethylene-α-olefin copolymer according to an exemplary embodiment of the present invention, a preferred range of the ratio between the indene-based transition metal compound of the present invention and an aluminum compound as a cocatalyst may be 1:1 to 2,000, based on a mole ratio of the transition metal (M): aluminum atom (Al).

Specifically, in the transition metal catalyst composition for preparing an ethylene homopolymer or an ethylene-α-olefin copolymer according to an exemplary embodiment of the present invention, a preferred range of the ratio of the indene-based transition metal compound of the present invention, a tetraarylborate compound and an aluminum compound may be 1:0.1 to 100:1 to 2,000, preferably in a range of 1:0.5 to 30:10 to 1,000, more preferably in a range of 1:0.5 to 5:10 to 500, based on a mole ratio of the center metal (M):boron atom (B):aluminum atom (Al).

When the ratio of the indene-based transition metal compound of the present invention described above, a tetraarylborate compound and an aluminum compound is out of the above range, the amount of the cocatalyst is relatively small, such that activation of the transition metal compound is not completely achieved. Thus, the catalyst activity of the indene-based transition metal compound may not be sufficient, or the cocatalyst is used more than necessary to greatly increase production costs. Within the above range, excellent catalyst activity for preparing an ethylene homopolymer or an ethylene-α-olefin copolymer is represented, however, the range of the ratios may vary within the above range depending on the purity of the reaction.

Another aspect of the present invention for achieving the above object relates to a method for preparing an ethylene-based polymer selected from the group consisting of an ethylene homopolymer and an ethylene-α-olefin copolymer, using the transition metal catalyst composition for preparing an ethylene homopolymer or an ethylene-α-olefin copolymer.

The method for preparing the ethylene-based polymer using the transition metal catalyst composition for preparing an ethylene homopolymer or an ethylene-α-olefin copolymer, may proceed by bringing the indene-based transition metal catalyst, the catalyst activator, the cocatalyst, and ethylene or an α-olefin comonomers into contact in the presence of a suitable organic solvent. Here, the indene-based transition metal catalyst, the catalyst activator, the cocatalyst components, and the like may be added to a reactor separately, or each component may be mixed previously and added to a reactor, and mixing conditions such as an addition order, temperature or concentration are not particularly limited. In addition, the catalyst activator may include a tetraarylborate compound represented by Formula 1, and the cocatalyst may be one or a mixture of two or more selected from the group consisting of the aluminum compound and boron compound described above.

Specifically, the method for preparing an ethylene homopolymer or an ethylene-α-olefin copolymer according to an exemplary embodiment of the present invention may include: a) injecting a catalyst activator composition including the tetraarylborate compound represented by Formula 1 and an organic solvent used in the preparation step of the tetraarylborate compound, without a separation process; b) injecting a single active site catalyst solution including a Group 4 transition metal; c) injecting an aluminum compound solution; and d) injecting ethylene.

In the method for preparing an ethylene homopolymer or an ethylene-α-olefin copolymer according to an exemplary embodiment of the present invention, as described above, the tetraarylborate compound in a dissolved state is injected into the organic solvent used in the preparation step, which is advantageous in the continuous solution process, and is capable of solving the disadvantages caused by a solid catalyst activator. In addition, an aromatic hydrocarbon-based solvent such as toluene may not be used.

The method for preparing an ethylene homopolymer or an ethylene-α-olefin copolymer according to an exemplary embodiment of the present invention may further include e) injecting α-olefins.

A preferred organic solvent which may be used in the preparation method of the present invention may be an aliphatic hydrocarbon-based solvent, (C3-C20) hydrocarbons, and a specific example thereof may be one or a mixed solvent of two or ore more selected from linear aliphatic hydrocarbon-based solvents such as butane, isobutane, pentane, hexane, heptane, octane, isooctane, nonane, decane and dodecane; and cyclic aliphatic hydrocarbon-based solvents such as cyclopentane, methylcyclopentane, cyclohexane, and methylcyclohexane.

The organic solvent which may be used in the preparation method may be an aromatic hydrocarbon-based solvent.

Specifically, when the ethylene homopolymer is prepared, ethylene is used alone as a monomer, in which appropriate ethylene pressure may be 1 to 1,000 atm, more preferably 6 to 150 atm. In addition, a polymerization reaction temperature of 25° C. to 220° C., preferably 70° C. to 220° C., and more preferably 100° C. to 220° C. is effective.

In addition, when an ethylene-α-olefin copolymer is prepared, C3-C18 α-olefins; C4-C20 diolefins; C5-C20 cycloolefins or cyclodiolefins; styrene and a derivative thereof may be used as a comonomer together with ethylene. Further, a preferred example of C3-C18 α-olefins may be selected from the group consisting of propylene, 1-butene, 1-pentene, 4-methyl-1-pentene, 1-hexene, 1-octene, 1-decene, 1-dodecene, 1-hexadecene, and 1-octadecene, a preferred example of C4-C20 diolefins may be selected from the group consisting of 1,3-butadiene, 1,4-pentadiene and 2-methyl-1,3-butadiene, and a preferred example of C5-C20 cycloolefins or cyclodiolefins may be selected from the group consisting of cyclopentene, cyclohexene, cyclopentadiene, cyclohexadiene, norbornene, 5-vinylidene-2-norbornene(VNB), 5-methylene-2-norbornene(MNB), and 5-ethylidene-2-norbornene(ENB). In the present invention, the olefin described above may be homopolymerized or two or more olefins may be copolymerized. In this case, preferred ethylene pressure and polymerization reaction temperature may be identical to those in the preparation of the ethylene homopolymer, and the ethylene-based copolymer prepared according to the method of the present invention usually contains in the range of 30 wt % or more of ethylene, preferably 60 wt % or more of ethylene, and more preferably 60 to 99 wt % of ethylene.

As described above, when the transition metal catalyst composition of the present invention is used, polymers in a scope from an elastomer to a high density polyethylene (HDPE), having a density of 0.850 g/cc to 0.960 g/cc and a melt flow rate of 0.001 to 2,000 dg/min may be easily and economically prepared, by appropriately using ethylene and C3-C10 α-olefins as a comonomer.

In addition, an ethylene/propylene (EP) elastomer and an ethylene/propylene/diene (EPDM) elastomer may be well prepared, using the transition metal catalyst composition of the present invention. In particular, since a high-priced diene is easily injected, an EPDM product having a Mooney viscosity (ASTM D1646-94, ML1+4@125° C.) adjusted to 1 to 250, preferably 10 to 200 may be easily prepared in an economical manner.

Further, in order to adjust a molecular weight when preparing the ethylene homopolymer or copolymer according to the present invention, hydrogen may be used as a molecular weight regulator, and the polymer usually has a weight average molecular weight (Mw) in a range of 5,000 to 1,000,000 g/mol.

Since the transition metal catalyst composition presented in the present invention is present in a homogeneous form in a polymerization reactor, it is preferred to apply the transition metal catalyst composition to a solution polymerization process which is carried out at a temperature equal to or more than a melting point of the polymer. However, as disclosed in U.S. Pat. No. 4,752,597, the catalyst composition may also be used in a slurry polymerization or gas phase polymerization process as a heterogeneous catalyst system by supporting the indene-based transition metal compound, the catalyst activator and the cocatalyst on a porous metal oxide support.

Hereinafter, the present invention will be described in detail by the following Examples, however, the scope of the present invention is not limited thereto.

Unless otherwise stated, all experiments of synthesizing ligands and catalysts were carried out using a standard Schlenk or glove box technology under a nitrogen atmosphere, and an organic solvent used in the reaction was refluxed under a sodium metal and benzophenone to remove moisture, and used after being distilled immediately before use. The $^1$H NMR analysis of the synthesized compound was carried out using Bruker 500 MHz at room temperature (25° C.)

Cyclohexane as a polymerization solvent was used after sufficiently removing moisture, oxygen, and other catalyst poisoning materials therefrom by passing cyclohexane through a 5 Å molecular sieve and a tube filled with active alumina, and bubbling cyclohexane with high purity nitrogen. The polymerized polymer was analyzed by the method described below:
1. Melt Flow Index (MI)
Measured according to ASTM D 2839.
2. Density
Measured according to ASTM D 1505, using a density gradient tube.
3. C2 Conversion (%) Analysis
Content ratios of unreacted ethylene and nitrogen as a standard material were measured using gas chromatography (GC).
4. Molecular Weight and Molecular Weight Distribution
Measured at 135° C. and at a rate of 1.0 mL/min, in a 1,2,3-trichlorobenzene solvent, using PL210 GPC equipped with PL Mixed-BX2+preCol, the molecular weight being corrected using a PL polystyrene standard material.

(Preparation Example 1) Preparation of Complex 1

Preparation of Compound 1-a

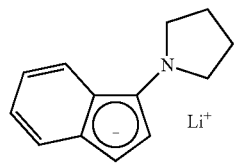

1-a (Preparation Example 1) Preparation of Complex 1

Preparation of Compound 1-b

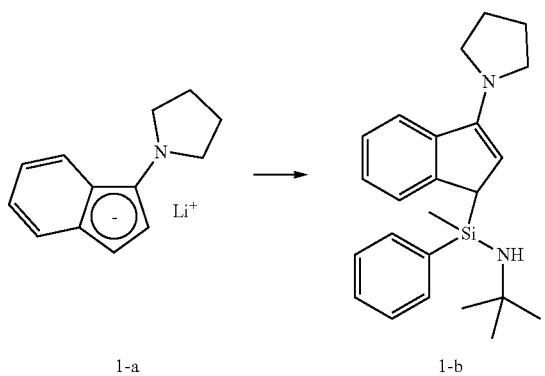

Under the nitrogen atmosphere, Compound 1-a (6.00 g, 31.4 mmol) was added to a 250 mL round bottom flask, and 150 mL of anhydrous tetrahydrofuran (THF) was added thereto and the mixture was stirred. N-tert-butyl-1-chloro-1-methyl-1-phenylsilaneamine (7.16 g, 31.4 mmol) was added by dissolving in tetrahydrofuran (THF) (50 mL), and then the mixture was stirred at room temperature for 12 hours. The solvent was removed in vacuo and dissolved by adding normal hexane (150 mL), and then the solids were removed with a filter filled with dried celite. The solvents were all removed to obtain Compound 1-b as a viscous oil (10.8 g, yield: 91.0%, a ratio of diastereomers 1:1).

$^1$H-NMR (500 MHz, $C_6D_6$, ppm): δ 0.156 (d, 3H), 0.703-0.830 (m, 1H), 0.976 (d, 9H), 1.501-1.528 (m, 4H), 3.089-3.217 (m, 4H), 3.501-3.604 (m, 1H), 5.259 (d, 1H), 7.034-7.652 (m, 9H)

Preparation of Complex 1

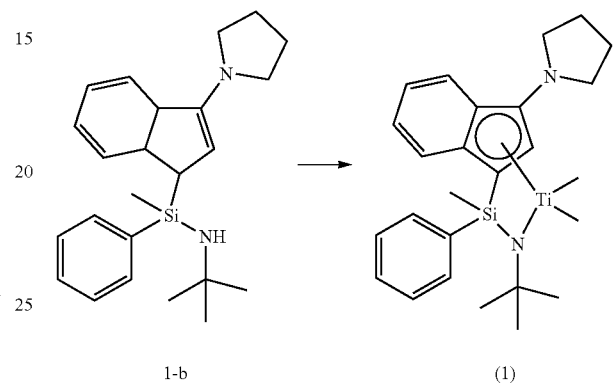

Under the nitrogen atmosphere, Compound 1-b (4.14 g, 11.0 mmol) was dissolved in diethyl ether (50 mL) in a 250 mL three neck round bottom flask, the temperature was cooled to −78° C., and then 1.5 M methyl lithium (29.4 mL, 44.2 mmol) was slowly injected thereinto. Then, the temperature was raised to room temperature, followed by stirring for 6 hours. The reactant was again cooled to −78° C., and then a solution of titanium(IV) chloride(TiCl$_4$) (2.1 g, 11.0 mmol) diluted with anhydrous normal hexane (30 mL) was slowly added thereto at −78° C. The reactant was stirred at room temperature for 3 hours, and then the solvent was removed in vacuo. The reactant was dissolved in normal hexane (100 mL) again, and the solid content was removed by a filter filled with dried celite. The solvents were all removed to obtain Complex 1 in a red (4.14 g, yield: 83.2%, a ratio of diastereomers~1:3).

$^1$H-NMR (500 MHz, $C_6D_6$, ppm): δ 0.153 (d, 3H), 0.702-0.950 (m, 6H), 1.490 (d, 9H), 2.951-3.442 (m, 8H), 5.360 (d, 1H), 6.698-7.890 (m, 9H)

Example 1

Preparation of N-octadecyl-N-octadecylideneanilinium tetrakis(pentafluorophenyl) borate [$C_{17}H_{35}$—C=N$^+$ ($C_{18}H_{37}$) ($C_6H_5$) B ($C_6F_5$)$_4^-$]

3 g (3.25 mmol) of trityl tetrakis(pentafluorophenyl) borate was added to a 1 L round bottom flask in a glovebox. Then, 300 g of cyclohexane was added to the round bottom flask and the mixture was stirred at room temperature to prepare a yellow suspension. 1.95 g (3.26 mmol) of N,N-dioctadecylaniline as a solid was added to the suspended solution, followed by stirring at room temperature for 30 minutes. Once the suspended solution turned clear, it was used in the subsequent copolymerization reaction without further separation.

$^1$H-NMR (500 MHz, CDCl$_3$, ppm): δ 0.86-0.89 (m, 6H), 1.22-1.32 (m, 62H), 1.44-1.51 (m, 2H), 3.43-3.47 (m, 2H), 7.05-7.58 (m, 5H), 7.64-7.68 (m, 1H).

Copolymerization of ethylene and 1-octene by continuous solution process

Copolymerization of ethylene and 1-octene was carried out using continuous polymerization equipment, as follows: The Complex 1 synthesized in Preparation Example 1 was used as a single active site catalyst, cyclohexane was used as a solvent, and the used amount of the catalyst was as described in the following Table 1. Ti input represents Complex 1 input synthesized in Preparation Example 1, Al input represents triisobutylaluminum input, and the catalyst activator input represents N-octadecyl-N-octadecylideneanilinium tetrakis(pentafluorophenyl) borate input synthesized in Example 1, respectively. Complex 1 was injected by dissolving in cyclohexane at a concentration of 0.3 g/L, triisobutylaluminum was injected in cyclohexane at a concentration of 3 g/L, N-octadecyl-N-octadecylideneanilinium tetrakis(pentafluorophenyl) borate was injected by dissolving in cyclohexane at a concentration of 3 g/L, and 1-octene was used as the comonomer to carry out synthesis. The C2 conversion of the reactor was able to be assumed by the reaction condition and the temperature gradient in the reactor when polymerization was carried out with one polymer under each reaction condition. The molecular weight was controlled by the function of the reactor temperature and the 1-octene content, and the conditions and the results are shown in the following Table 1.

Comparative Example 1

Copolymerization of ethylene and 1-octene by continuous solution process

Copolymerization of ethylene and 1-octene was carried out using continuous polymerization equipment, as follows: The Complex 1 synthesized in Preparation Example 1 was used as a single active site catalyst, cyclohexane was used as a solvent, and the used amount of the catalyst was as described in the following Table 1. Ti input represents Complex 1 input synthesized in Preparation Example 1, Al input represents triisobutylaluminum input, and the catalyst activator input represents trityl tetrakis(pentafluorophenyl) borate (TTB) input, respectively. Complex 1 was injected by dissolving in toluene at a concentration of 0.1 g/L, triisobutylaluminum and TTB were injected by dissolving in toluene at a concentration of 1 g/L using the composition of Table 1 below, and 1-octene was used as the comonomer to carry out synthesis. The C2 conversion of the reactor was able to be assumed by the reaction condition and the temperature gradient in the reactor when polymerization was carried out with one polymer under each reaction condition. The molecular weight was controlled by the function of the reactor temperature and the 1-octene content, and the conditions and the results are shown in the following Table 1.

TABLE 1

| | | Example 2 | Comp. Example 1 |
|---|---|---|---|
| Polymerization conditions | Single active site catalyst | Preparation Example 1 (Complex 1) | Preparation Example 1 (Complex 1) |
| | Catalyst activator | Example 1 | TTB |
| | Total solution flow rate (Kg/h) | 5 | 5 |
| | Ethylene input (wt %) | 10 | 10 |
| | Input mole ratio of 1-octene and ethylene (1-C8/C2) | 1.5 | 1.5 |
| | Ti input (μmol/kg) | 6.4 | 10 |
| | Al input (μmol/kg) | 200 | 200 |
| | Catalyst activator input (μmol/kg) | 19 | 30 |
| | Reaction temperature (° C.) | 180 | 180 |
| Polymerization results | C2 conversion rate (%) | 90 | 90 |
| | MI | 0.28 | 0.32 |
| | Density (g/cc) | 0.885 | 0.887 |

Ti: refers to Ti in the single active site catalyst (Preparation Example 1)
Al: refers to Al in a cocatalyst, an aluminum compound, i.e., triisobutylaluminum.
B: refers to B in an activator, Example 1 (N-octadecyl-N-octadecylideneanilinium tetrakis(pentafluorophenyl) borate) or TTB (trityl tetrakis(pentafluorophenyl) borate).

As shown in the above Table 1, it was confirmed that Example 2 in which polymerization was carried out with the catalyst composition according to the present invention was able to easily prepare a high molecular weight ethylene-based copolymer having a high conversion rate of ethylene, low density and a low MI value meaning a high molecular weight even under the condition of high temperature (180° C. or more). In addition, it was confirmed that Example 2 showed an equivalent level of ethylene conversion despite the use of a small amount of catalyst as compared to Comparative Example 1, so that the catalyst composition according to the present invention exerted an excellent effect on the activation of a single active site catalyst.

In particular, a novel tetraarylborate compound according to the present invention may be dissolved in an aliphatic hydrocarbon-based solvent such as cyclohexane, but not an aromatic hydrocarbon-based solvent, depending on the selection of the cation of the alkylideneanilinium structure. Due to such solubility, the transition metal catalyst composition according to the present invention may not only facilitate the operation of a commercial process by providing a solution-type catalyst activator including an aliphatic hydrocarbon-based solution but also solve the disadvantages caused by the solid catalyst activator.

As described above, though the present invention has been described in detail with respect to the exemplary embodiments thereof, a person skilled in the art may make various variations of the present invention without departing from the spirit and the scope of the present invention, as defined in the claims which follow.

The invention claimed is:

1. A tetraarylborate compound represented by Formula 1:

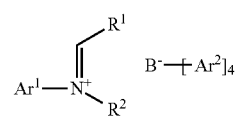

[Formula 1]

wherein

B is a boron atom;

Ar1 is (C6-C30) aryl, wherein the aryl of Ar1 may be further substituted by one or more substituents selected from the group consisting of (C1-C30) alkyl, halo (C1-C30) alkyl, and (C6-C30) aryl (C1-C30) alkyl;

Ar2 is fluorine-substituted (C6-C30) aryl;

R1 is hydrogen or (C1-C30) alkyl; and

R2 is (C1-C30) alkyl, or R2 and R1 are optionally linked to each other to form a ring, wherein the ring may be further substituted by one or more substituents selected from the group consisting of (C1-C30) alkyl, (C1-C30)

alkoxy, halo (C1-C30) alkyl, (C3-C30) cycloalkyl, (C1-C30) alkyl (C6-C30) aryl, (C6-C30) aryl, (C6-C30) aryloxy, (C1-C30) alkyl (C6-C30) aryloxy, (C6-C30) aryl (C1-C30) alkyl, and ((C1-C30) alkyl (C6-C30) aryl) (C1-C30) alkyl.

2. The tetraarylborate compound of claim 1, wherein the tetraarylborate compound is represented by Formula 2:

[Formula 2]

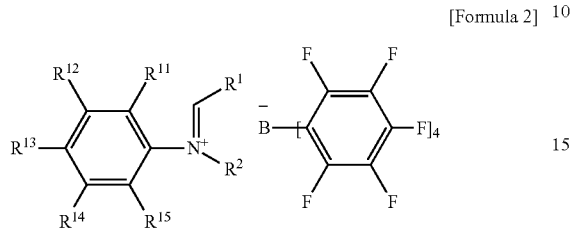

wherein

B, R1 and R2 are as defined in Formula 1 of claims 1; and $R^{11}$ to $R^{15}$ are each independently hydrogen, (C1-C30) alkyl, halo (C1-C30) alkyl, or (C6-C30) aryl (C1-C30) alkyl.

3. The tetraarylborate compound of claim 1, wherein at least one selected from R1 and R2 is (C8-C30) alkyl.

4. The tetraarylborate compound of claim 1, wherein R1 and R2 are each independently (C12-C30) alkyl.

5. A transition metal catalyst composition for preparing an ethylene homopolymer or an ethylene-α-olefin copolymer, comprising:
the tetraarylborate compound of claim 1;
a single site catalyst complex including a Group 4 transition metal; and
an aluminum compound.

6. The transition metal catalyst composition of claim 5, wherein the single site catalyst complex is a metallocene catalyst.

7. The transition metal catalyst composition of claim 5, wherein the single site catalyst complex is an indenyl-based transition metal compound represented by Formula A:

[Formula A]

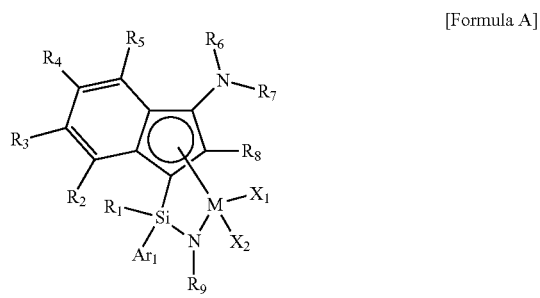

wherein

M is a Group 4 transition metal in the periodic table;
$R_1$ is (C1-C30) alkyl or (C2-C20) alkenyl, wherein the alkyl or alkenyl of R1 is optionally further substituted by one or more substituents selected from the group consisting of halogen, (C6-C30) aryl, and (C1-C30) alky (C6-C30) aryl;
$Ar_1$ is (C6-C30) aryl, wherein the aryl of $Ar_1$ is optionally further substituted by one or more substituents selected from the group consisting of (C1-C30) alkyl, halo (C1-C30) alkyl, and (C6-C30) aryl (C1-C30) alkyl;

$R2$ to $R_5$ are each independently hydrogen, (C1-C30) alkyl, (C1-C30) alkoxy, halo (C1-C30) alkyl, (C3-C20) cycloalkyl, (C1-C30) alkyl (C6-C30) aryl, (C6-C30) aryl, (C6- C30) aryloxy, (C1-C30) alkyl (C6-C30) aryloxy, (C6-C30) aryl (C1-C30) alkyl, or ((C1- C30) alkyl (C6-C30) aryl) (C1-C30) alkyl, or R2 to R5 are linked to an adjacent substituent to form a fused ring, wherein the fused ring may beis optionally further substituted by one or more substituents selected from the group consisting of (C1-C30) alkyl, (C1-C30) alkoxy, halo (C1- C30) alkyl, (C3-C20) cycloalkyl, (C1-C30) alkyl (C6-C30) aryl, (C6-C30) aryl, (C6-C30) aryloxy, (C1-C30) alkyl (C6-C30) aryloxy, (C6-C30) aryl (C1-C30) alkyl, and ((C1-C30) alkyl (C6-C30) aryl) (C1-C30) alkyl;

R9 is (C1-C30) alkyl, (C3-C20) cycloalkyl or (C6-C30) aryl (C1-C30) alkyl;

R6 and R7 are each independently (C1-C30) alkyl, halo (C1-C30) alkyl, (C3- C20) cycloalkyl, (C6-C30) aryl, (C1-C30) alkyl (C6-C30) aryl, (C1-C30) alkoxy (C6-C30) aryl or (C6-C30) aryl (C1-C30) alkyl, or R6 and R7 may beare optionally linked to each other to form a ring, wherein the ring may beis optionally further substituted by one or more substituents selected from the group consisting of (C1-C30) alkyl, halo (C1-C30) alkyl, (C6-C30) aryl (C1-C30) alkyl, (C1-C30) alkoxy, (C3-C20) cycloalkyl, (C6-C20) aryl, (C1-C30) alkyl (C6-C30) aryl and (C6- C20) aryloxy;

R8 is hydrogen or (C1-C30) alkyl;

$X_1$ and $X_{b\ 2}$ are each independently halogen, (C1-C30) alkyl, (C2-C20) alkenyl, (C3-C20) cycloalkyl, (C6-C30) aryl, (C6-C30) aryl (C1-C30) alkyl, ((C1-C30) alkyl (C6-C30) aryl) (C1-C30) alkyl, (C1-C30) alkoxy, (C6-C30) aryloxy, (C1-C30) alkyl (C6-C30) aryloxy, (C1-C30) alkoxy (C6-C30) aryloxy, $-OSiR^a R^b R^c$, $-SR^e$, $-NR^e R^f$, $-PR^g R^h$, or (C1-C30) alkylidene;

$R^a$ to $R^d$ are each independently (C1-C30) alkyl, (C6-C20) aryl, (C6-C20) aryl (C1-C30) alkyl, (C1-C30) alkyl (C6-C20) aryl, or (C3-C20) cycloalkyl; and $R^e$ to $R^h$ are each independently (C1-C30) alkyl, (C6-C20) aryl, (C6-C20) aryl (C1-C30) alkyl, (C1-C30) alkyl (C6-C20) aryl, (C3-C20) cycloalkyl, tri (C1-C30) alkylsilyl, or tri (C6-C20) arylsilyl;

with a proviso that when one of $X_1$ and $X_2$ is (C1-C30) alkylidene, the other one is ignored.

8. The transition metal catalyst composition of claim 5, wherein the aluminum compound is one or more selected from the group consisting of alkylaluminoxane and organic aluminum.

9. The transition metal catalyst composition of claim 5, wherein a ratio of the single site catalyst and a tetraarylborate compound is in a range of 1:0.1 to 100, based on a mole ratio of the transition metal (M): boron atom (B).

10. The transition metal catalyst composition of claim 5, wherein a ratio of the single active site catalyst complex, the tetraarylborate compound and the aluminum compound is in a range of 1:0.1 to 100:1 to 2,000, based on a mole ratio of the transition metal (M): boron atom (B): aluminum atom (Al).

11. The transition metal catalyst composition of claim 10, wherein a ratio of the single site catalyst complex, the tetraarylborate compound and the aluminum compound is in a range of 1:0.5 to 5:10 to 500, based on a mole ratio of the transition metal (M): boron atom (B): aluminum atom (Al).

12. A method for preparing an ethylene homopolymer or an ethylene-α-olefin copolymer, in the presence of the transition metal catalyst composition of claim 5.

13. The method of claim 12, wherein the a-olefin is one or a mixture of two or more selected from the group consisting of propylene, 1-butene, 1-pentene, 1-hexene, 1-heptene, 1-octene, 1-decene, 1-undecene, 1-dodecene, 1-tetradecene, 1-hexadecene, 1-itocene, 3-butadiene, 1,4-pentadiene, and 2-methyl-1,3-butadiene, and an ethylene content in the ethylene-α-olefin copolymer is 30 to 99 wt %.

14. The method of claim 13, further comprising one or a mixture of two more selected from the group consisting of cyclopentene, cyclohexene, cyclopentadiene, cyclohexadiene, norbornene, 5-vinylidene-2-norbornene, 5-methylene-2-norbornene, 5-ethylidene-2-norbornene, and styrene, as a comonomer polymerized with the ethylene.

15. The method of claim 12, wherein a pressure in a reactor for homopolymerization of ethylene or copolymerization of ethylene and an α-olefin is 6 to 150 atm, and polymerization reaction temperature is 50 to 200° C.

* * * * *